(12) United States Patent
Baccelli et al.

(10) Patent No.: US 9,393,051 B2
(45) Date of Patent: Jul. 19, 2016

(54) DEVICE FOR TENSIONING A FLEXIBLE STRIP AND ASSEMBLY COMPRISING SUCH A DEVICE WITH FLEXIBLE STRIP

(71) Applicant: Implanet, Societe Anonyme, Martillac (FR)

(72) Inventors: Christian Baccelli, Saucats (FR); Regis Le Couedic, Bordeaux (FR)

(73) Assignee: Implanet, Societe Anonyme, Martillac (FR)

( * ) Notice: Subject to any disclaimer, the term of this patent is extended or adjusted under 35 U.S.C. 154(b) by 0 days.

(21) Appl. No.: 14/350,387

(22) PCT Filed: Oct. 25, 2012

(86) PCT No.: PCT/FR2012/052454
§ 371 (c)(1),
(2) Date: Apr. 8, 2014

(87) PCT Pub. No.: WO2013/060990
PCT Pub. Date: May 2, 2013

(65) Prior Publication Data
US 2014/0277207 A1    Sep. 18, 2014

(30) Foreign Application Priority Data
Oct. 28, 2011    (FR) .................................... 11 03319

(51) Int. Cl.
*A61B 17/70* (2006.01)
*A61B 17/88* (2006.01)

(52) U.S. Cl.
CPC ......... *A61B 17/7053* (2013.01); *A61B 17/8869* (2013.01)

(58) Field of Classification Search
USPC .................................................. 606/74, 103
See application file for complete search history.

(56) References Cited

U.S. PATENT DOCUMENTS

| 1,346,940 | A | 7/1920 | Collins |
| 6,146,386 | A | 11/2000 | Blackman et al. |
| 6,443,955 | B1 * | 9/2002 | Ahrend .............. A61B 17/8866 606/103 |

(Continued)

FOREIGN PATENT DOCUMENTS

| EP | 1878397 A1 | 1/2008 |
| WO | 8401101 A1 | 3/1984 |
| WO | 2007034112 A1 | 3/2007 |

OTHER PUBLICATIONS

International Search Report of PCT/FR2012/052454 dated Dec. 19, 2012.

(Continued)

*Primary Examiner* — Jan Christopher Merene
(74) *Attorney, Agent, or Firm* — Banner & Witcoff, Ltd.

(57) ABSTRACT

This is a system and an assembly for tensioning a flexible strip (3) to hold a bony element on an implant, comprising a shank (15) and means (42) for adjustably immobilizing a component (29) that is capable of translational movement with respect to a portion (25) of the device. The shank (15) comprises a handle (23) for gripping at its second end (24), the portion (25) of the device (14) making an angle with the shank (15), the flexible strip (3) having two free ends. The component (29) capable of movement comprises a wheel (31) free to rotate with respect to a pivot pin (32) perpendicular to the portion (25), for guiding the strip (3) around its rounded periphery (33) comprising two distinct elements (34, 35) for anchoring the flexible strip (3).

15 Claims, 2 Drawing Sheets

(56) References Cited

U.S. PATENT DOCUMENTS

| | | | |
|---|---|---|---|
| 8,128,635 B2 | 3/2012 | Belliard et al. | |
| 8,162,946 B2 | 4/2012 | Baccelli et al. | |
| 8,728,083 B2* | 5/2014 | Baccelli | A61B 17/7053 606/86 A |
| 9,113,963 B2 | 8/2015 | Baccelli et al. | |
| 2005/0228375 A1* | 10/2005 | Mazda | A61B 17/707 606/263 |
| 2005/0240198 A1* | 10/2005 | Albertson | A61B 17/8076 606/103 |
| 2009/0082821 A1* | 3/2009 | Konno | A61B 17/8861 606/86 A |
| 2009/0105715 A1 | 4/2009 | Belliard et al. | |
| 2009/0138048 A1* | 5/2009 | Baccelli | A61B 17/8869 606/263 |
| 2012/0271354 A1* | 10/2012 | Baccelli | A61B 17/7053 606/263 |
| 2013/0261680 A1* | 10/2013 | Baccelli | A61B 17/7053 606/86 A |
| 2014/0114356 A1* | 4/2014 | Le Couedic | A61B 17/842 606/263 |
| 2014/0277207 A1* | 9/2014 | Baccelli | A61B 17/8869 606/86 A |

OTHER PUBLICATIONS

International Search Report mailed Apr. 4, 2012 in related International Application No. PCT/FR2011/000639.

* cited by examiner

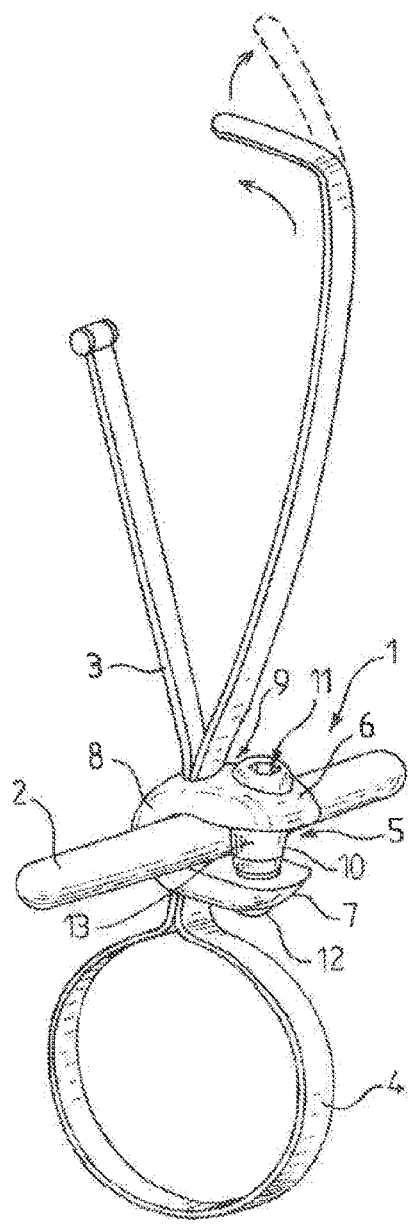
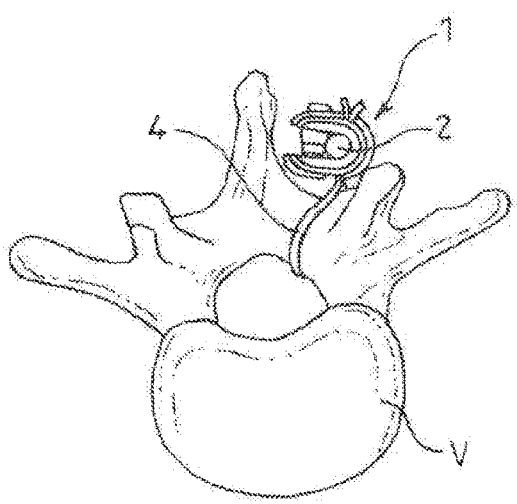
FIG.2
FIG.1

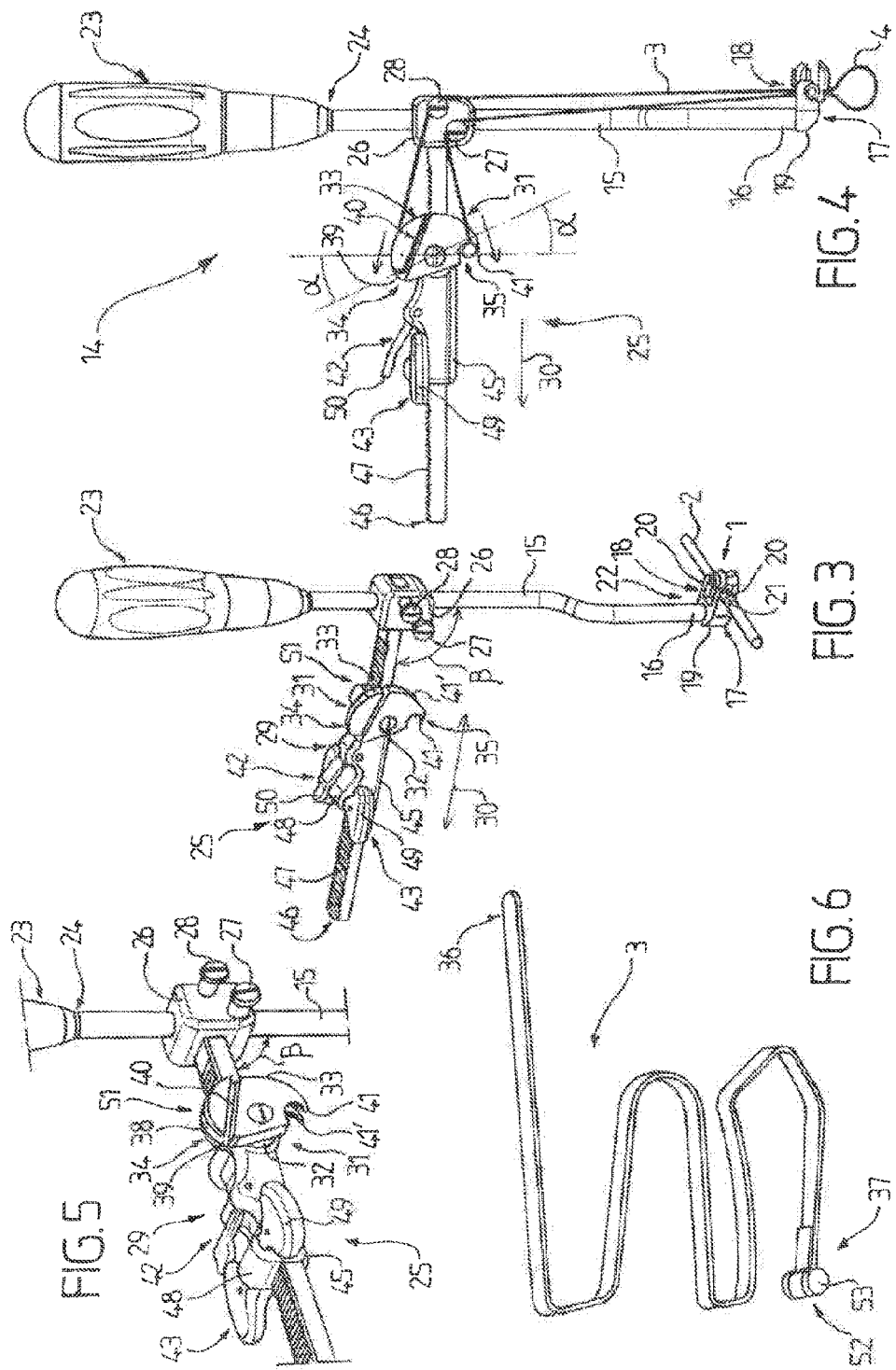

DEVICE FOR TENSIONING A FLEXIBLE STRIP AND ASSEMBLY COMPRISING SUCH A DEVICE WITH FLEXIBLE STRIP

The present invention relates to a device for tensioning a flexible strip to hold a bone element on an implant, having a rod with a first end provided with means for bearing on a longitudinal bar for fixing the implant, a movable component for fastening the flexible strip to a portion of the device, and adjustable blocking means for blocking the movable component in translation with respect to this portion.

It also relates to an assembly comprising such a device and the flexible strip that goes with it.

It is applicable particularly, but not exclusively, in the field of straightening the spinal column of a patient presenting an abnormal curvature.

In this case, with the vertebrae not being correctly aligned relative to one another with respect to the vertebral axis, they present mutual inclinations.

In order to straighten the whole, it is known to place at a substantially equivalent distance from the lateral edges of the vertebrae, on each side of the spinal column, by way of longitudinal bars connecting them, either screws, which are inserted into the vertebrae themselves, or hooks, which are introduced along the vertebral canal.

However, such devices have disadvantages because they are aggressive.

To mitigate these disadvantages, a flexible link has been proposed for fixing the vertebra to the connecting component, which is itself fixed to the longitudinal bar permitting the straightening.

Means for blocking the flexible link by reclosing the connecting component on the bar are then necessary.

The problem that the invention aims to solve here is that of tensioning this flexible link for fixing the vertebra to the connecting component.

In practice, it is important for the user, when fitting this link in place, to be able to gradually retighten the latter without in any way damaging the bone element which will then be compressed by the flexible strip.

Ancillary tensioning devices are currently available that are provided with a rod, a component that is movable in translation along the rod, and an element mounted on the movable component and tending horizontally to separate the end of the rod from the component.

However, such an ancillary device has disadvantages.

It in fact entails pulling in the continuation of the link itself, which has to be twisted in order to permit its tensioning.

Furthermore, no manual feedback of the tension is possible with such an instrument, which thus requires, in order to avoid crushing the bone element, an adjustable dynamometric system making it possible to stop the tensioning beyond a certain determined value.

The present invention aims to make available a device for tensioning a flexible strip that responds better than those previously known to the requirements that arise in practice, especially in that it will allow much greater flexibility, better sensitivity to the degree of tensioning because of the very design of the tools used for such tensioning, and in that it has much improved and simple adjustment possibilities.

The invention also makes it possible to compensate for the resistances generated by defects in the sliding of the flexible strip around the anatomical attachment.

To this end, the invention proposes in particular a device for tensioning a flexible strip to hold a bone element on an implant, having a rod with a first end provided with means for bearing on a longitudinal bar for fixing the implant, a movable component for fastening the flexible strip to a portion of the device, and adjustable blocking means for blocking the movable component in translation with respect to said portion of the device, characterized in that the rod comprises a handle for gripping at its second end, in that said portion of the device forms an angle with the rod to which it is rigidly fixed at an intermediate level with angular return of the strip, and in that, with said flexible strip comprising two free ends, said movable component comprises a wheel free in rotation with respect to an axis perpendicular to said portion, for guiding the strip around its rounded periphery comprising two distinct elements for anchoring the flexible strip, namely a first element for one of said ends of the flexible strip, and a second element for the other end.

The manual turnable means for actuating the movable component, which is itself offset on a lateral branch forming an angle, permit gradual and controlled tensioning of the flexible strip.

Advantageously, the bearing means are on each side of the implant with respect to the rod.

In advantageous embodiments, recourse is also made to one or more of the following arrangements:
  the two anchoring elements are substantially diametrically opposite;
  the wheel is in the shape of a truncated circular or oval disk having, on its periphery, a groove for guiding the strip;
  with the strip having at one side a flexible blade-shaped end-piece and, at the other side, a fastening peg, the first element is formed by an oblique cutting in the plane of the wheel for retention of the blade, and the second element is formed by a hook for fastening the peg;
  the adjustable blocking means comprise turnable means suitable for actuating the movable component;
  the adjustable blocking means have a rack rigidly connected to the device portion, and the turnable means comprise a non-return ratchet system with actuating key rigidly connected to the movable component;
  the ratchet system has a lever arm for releasing the ratchet;
  the turnable means have at least one wing element (grip);
  the device has a connecting component disposed between the rod and the device portion and formed by a block provided with two sprocket wheels with mutually parallel axes for angular return of said strip in its plane, said block being rigidly connected to said rod;
  the connecting component is movable along the rod;
  the angle of said device portion with respect to the rod is adjustable;
  the angle of said device portion with respect to the rod is between 90° and 130°;
  the angle of said device portion with respect to the rod is 90°.

The invention also makes available an assembly comprising a device of the kind described above and a flexible strip.

It also relates to a method for tensioning a strip on a bone and/or a vertebra using an assembly of the kind described above.

The invention will be better understood from reading the following description of an embodiment given hereinbelow as a non-limiting example.

The description makes reference to the attached drawings, in which:

FIG. 1 is a perspective view of a body for fixing on a bar, using a flexible strip that is able to be tensioned with the device according to the invention (in order to hold a bone element).

FIG. 2 is a bottom view of a vertebra showing the fixing body on the bar and the flexible strip sectioned after the strip has been tensioned by the device according to the invention.

FIG. 3 is an axonometric perspective view of the device according to one embodiment of the invention.

FIG. 4 is a side view of an assembly comprising the device from FIG. 3 and a flexible strip.

FIG. 5 is a partial perspective view of the movable component of the device from FIG. 3.

FIG. 6 is a perspective view of a flexible connecting strip according to one embodiment of the invention.

In the description below, the same reference numbers will be used to designate the same elements.

FIG. 1 shows a body 1 for fixing on a cylindrical bar 2, and a flexible strip 3 made of braided polymer, for example of polyester, measuring 6 mm in width and 30 cm in length in order to form the loop 4.

Adjustable means 5 for blocking the flexible strip 3 on the fixing body 1 are provided. The fixing body 1 is, for example, formed by a one-piece component that forms a clamp with a U-shaped cross section, said U comprising two thick branches 6, 7 which have a cross section substantially in the shape of a half oval and which are symmetrical with respect to a longitudinal plane and are connected to each other by a connecting part 8 in the form of a toroidal half-ring which, on one side, forms the semi-cylindrical bottom of the U and, on the other side, forms the rounded outer walls of the branches 6 and 7.

The bottom wall of the U is of a shape complementing or substantially complementing that of the bar 2.

Each branch 6, 7 has an aperture 9, for example in the form of a wide slit, for example five to ten times wider than the thickness of the braid, in order to facilitate introduction of the latter during the operation.

Each branch 6 and 7 has a cylindrical orifice for the passage of the blocking means 5, namely a bore of diameter D and a tapped cylindrical orifice for screwing of diameter d<D.

The blocking means 5 are formed by a connecting component 10, or screw, provided on one side with a head 11 for engaging in the bore of the U and on the other side with an end 12 for screwing into said facing tapped cylindrical orifice.

In the embodiment more particularly described here, the head of the screw 11 comprises a cylindrical upper part and a downwardly tapering lower part 13, designed to compress the bar 2 as the component is screwed in.

FIG. 2 shows the vertebra V as fixed via the loop 4 to the bar 2 via the body 1 in order to permit tensioning of the loop 4 on the bone V by a device 14 as shown in FIGS. 3, 4 and 5.

The device 14 for tensioning the flexible strip 3 via the loop 4 has a slender rod 15, which is 40 cm in length for example, is cylindrical and is provided at a first end 16 with bearing means 17 consisting, for example, of a part rigidly connected to the end 16 having a part 18 in the form of cylindrical hooks, of a shape complementing and designed to cooperate with the bar 2.

More specifically, the component 17 is, for example, formed by a heel part 19 rigidly connected to the end 16 and extended on each side by two parallel symmetrical branches 20 which are provided at their ends with two shoulder parts 21 designed to cooperate with the bar 2.

The two branches 20 are themselves separated by an opening 22 into which is inserted the body 1 for fixing on the bar in a manner known per se.

The device has a handle 23 for manual gripping in the continuation of the rod 15, at the second end 24 thereof.

The device according to the embodiment of the invention more particularly described here also has a portion 25 forming an angle β with the rod 15, to which it is rigidly fixed at an intermediate level by way of a connecting component 26 disposed between rod and said portion and formed by a block which is, for example, substantially parallelepipedal and is provided with two sprocket wheels 27 and 28 with mutually parallel axes, perpendicular to the axis of the rod 15, for angular return of the strip 3 in its plane, toward the rod portion 25.

A component 29 which is movable in translation (arrow 30) with respect to the portion 25 is provided.

The movable component 29 additionally comprises a compensation wheel 31 mounted freely in rotation about an axis 32 connecting them, the axis 32 being perpendicular to the movement of the movable component 29 and positioning the edge 33 of the compensation wheel 31 and the two sprocket wheels 27, 28 opposite each other.

The compensation wheel 31 has the general shape of a truncated circular or ovoid disk and comprises means 34, 35 for anchoring the ends 36, 37 of the flexible strip 3 (see FIG. 6).

On its rounded periphery, it comprises a groove 38 which guides the flexible strip 3 and which has a width slightly greater than said flexible strip 3.

The anchoring means 34, 35, which allow the ends 36, 37 of the flexible strip 3 to be rigidly connected to the compensation wheel 31, are substantially diametrically opposite.

In the rest situation, that is to say when no tension is applied to the compensation wheel 31, the latter is balanced in such a way that the anchoring means 34, 35 are aligned vertically and approximately parallel to the axis of the rod 15.

At the end of the guide groove 38, the first upper anchoring means 34 comprises a return 39 formed by a cutting 40 in the compensation wheel 31.

The thickness of the cutting 40 is suitable for receiving and retaining the flexible strip 3 and crosses the surface of said compensation wheel 31.

The return thus balances the traction forces of the strip 3 and thereby ensures an optimum hold of said strip 3.

The second anchoring means 35 comprises two curved teeth 41, 41' adapted to cooperate with a cylinder and to keep the latter in place.

The two teeth 41, 41' are spaced apart by at least the width of the strip 3.

The movable component 29 additionally comprises adjustable means 42 which block the movable component 29 in its said translation and are provided with turnable means 43.

Referring more specifically to FIG. 5, the adjustable blocking means 42 comprise a rack rigidly connected to the portion 25, while the turnable means 43 for their part comprise a non-return ratchet system with actuation key rigidly connected to the movable component 29.

The adjustable blocking means 42 have a body 45 pierced with a bore through which passes the end 46 of the portion 25 which is fixed to the rod 15 by the connecting component 26.

The end 46, which has on its upper part the teeth 47 of the rack, will cooperate by gentle friction with the bore of the component 45 which has, in its upper part, a stub 48 pierced with a lateral bore through which passes the axis of the wings 49 for manually actuating a toothed wheel designed to cooperate with the teeth 47 of the rack in such a way that, when the wing grips are turned, the movable component 29 will move transversely along the portion 25.

Ratchet means known per se are designed to be able to be actuated and unlocked when the non-return lever 50 is lifted, in a manner known per se.

This makes it possible in practice to release the ratchet and to free the tension of the flexible strip.

The flexible strip 3 and more precisely the ends 36, 37 of this flexible strip 3 are rigidly connected to the compensation wheel 31 fixed to the end 51 of the movable component 29 in such a way that, when the movable component 29 is moved toward the outside of the rod 15, the strip 3 and the loop 4 are tensioned.

The angle β between the portion 25 and the rod 15 is, for example, adjustable in order to be blocked in a manner known per se.

The flexible strip 3 will now be described with reference to FIG. 6.

It has a generally parallelepipedal shape, with one of the ends 36 of the flexible strip 3 being able to be of a beveled shape, either pointed or rounded.

This same end 36 can be reinforced by a metal blade of the same shape as the end of the flexible strip 3, to which it is possible to give a malleable hook shape permitting the introduction and the passage under the vertebra.

At the other end 37 of the strip there is an anchoring means.

In the embodiment more particularly described here, the anchoring means consists of a fastening peg 52.

The fastening peg 52 is formed by a cylinder 53 orthogonal to the flexible strip 3 and comprising, on its central part, a groove which has a width slightly greater than the flexible strip 3 and around which a part of said flexible strip 3 is wound in such a way as to capture said cylinder 53.

The operation of a device according to the invention will now be described.

The user will first of all form the loop 4 around the bone element.

To do this, he firstly passes the first end 36 of the flexible strip 3 into the fixing body 6 and then passes it round the bone part and back through the fixing body 6, thereby forming a loop 4.

This operation is made easier by the profile of the end of the flexible strip 3 and also by its metallic reinforcement being of small dimensions and of a certain rigidity.

Then, in the cutting 40 of the compensation wheel 31, the user fixes the first end 36 to the first anchoring means 34 of the compensation wheel 31, resting the flexible strip 3 on the guide groove 38 of the compensation wheel 31.

One and the same end passes through the fixing body 32.

The loop 4 around the bone is therefore simple and does not involve a knot, which saves time for the surgeon and permits greater safety for this awkward and complex operation in a tissue environment.

He then fixes the second end 37 of the flexible strip 3 to the second anchoring means 35 by inserting the anchoring peg 52 of the end into the teeth 41, 41' of the anchoring means 35, passing the strip 3 through the space between the two teeth 41, 41' and resting it on the stub 27.

The user is therefore not obliged to fix the end of the flexible strip 3 in order to form a belt of some kind.

The anchoring peg 52 of the flexible strip 3 is retained by the inwardly curved shape of the teeth 41, 41' and by the cylinder 53 being clipped therein.

The balancing of the compensation wheel 31 thus makes it possible to avoid inducing parasitic forces on the tension of the flexible strip 3 and thus of the bone part.

The dimensioning of the flexible strip 3 will have been calculated beforehand in such a way that the strip 3 is almost in the tensioned position in the case where this is greater, it is also possible, for example in one embodiment, to move the component 26 for fixing the portion 25 on said rod 15 in such a way as to obtain the desired initial tension.

The tensioning is then effected by turning the wings 49, and this drives the toothed wheel 47, which meshes with the rack.

When the flexible strip 3 slides without resistance on the bone, the compensation wheel 31 acts as a rigid fixation of the ends of the flexible strip 3 and remains in its natural balancing position.

When the sliding of the flexible strip 3 is braked in its sliding, the corresponding strand experiences excess tension compared to the other strand, which imbalances the compensation wheel 31, which inclines by an angle α in order to compensate gradually for this resistance.

As is evident, and as also results from the foregoing, the present invention is not limited to the embodiments that are more particularly described. On the contrary, it encompasses all the variants thereof and especially those where there is only a single wing key, where the screwing means are different and/or where the anchoring means 34, 35 of the flexible strip 3 are formed differently.

The invention claimed is:

1. A device for tensioning a flexible strip to hold a bone element on an implant, having a rod with a first end provided with means for bearing on a longitudinal bar for fixing the implant, a movable component for fastening the flexible strip to a portion of the device, and adjustable blocking means for blocking the movable component in translation with respect to said portion of the device,
wherein the rod comprises a handle for gripping at its second end, the moveable component is located on said portion of the device, said portion forms a lateral branch rigidly fixed to the rod (15) adjacent an angle return for the strip, with said flexible strip comprising two free ends, said movable component comprises a wheel free in rotation relative to said portion about an axis perpendicular to said portion, for guiding the strip around its rounded periphery, said wheel comprising two distinct elements for anchoring said free ends of the flexible strip, namely a first element for anchoring one of said free ends of the flexible strip, and a second element for anchoring the other free end of the flexible strip.

2. The device as claimed in claim 1, wherein the first and second elements are substantially diametrically opposite from each other.

3. The device as claimed in claim 2, wherein the wheel is in the shape of a truncated circular or oval disk having, on its periphery, a groove for guiding the strip.

4. The device as claimed in claim 1, wherein the first element is formed by an oblique cutting in the plane of the wheel and the second element is formed by a hook.

5. The device as claimed in claim 1, wherein the adjustable blocking means comprise turnable means suitable for actuating the movable component.

6. The device as claimed in claim 5, wherein the adjustable blocking means has a rack rigidly connected to the device portion, and the turntable means comprise a non-return ratchet system with an actuating key rigidly connected to the movable component.

7. The device as claimed in claim 6, wherein the ratchet system has a releasing lever arm.

8. The device as claimed in claim 5, wherein the turntable means have at least one wing grip.

9. The device as claimed in claim 1, wherein the device has a connecting component piece disposed between the rod and said portion of the device and formed by a block provided with two sprocket wheels with mutually parallel axes for angular return of said strip in its plane, said block being rigidly connected to said rod.

10. The device as claimed in claim 9, wherein the connecting component piece is movable along the rod.

11. The device as claimed in claim 1, wherein the angle of said portion of the device with respect to the rod is adjustable.

12. The device as claimed in claim 1, wherein the angle of said portion of the device with respect to the rod is between 90° and 130°.

13. The device as claimed in claim 12, wherein the angle of said portion of the device with respect to the rod is 90°.

14. An assembly comprising a device as claimed in claim 1 and a flexible strip.

15. An assembly comprising a device as claimed in claim 4, with a strip having at one side a flexible blade-shaped endpiece and, at the other side, a fastening peg, the oblique cutting being configured for retaining the blade-shaped endpiece and the hook being configured for fastening the peg.

* * * * *